(12) United States Patent
Berry

(10) Patent No.: US 9,987,322 B1
(45) Date of Patent: Jun. 5, 2018

(54) TREATMENT OF PAIN IN PERIPHERAL NEUROPATHY USING TOPICAL HAMELIA PATENS EXTRACT

(71) Applicant: Don Wayne Berry, Georgetown, TX (US)

(72) Inventor: Don Wayne Berry, Georgetown, TX (US)

( * ) Notice: Subject to any disclaimer, the term of this patent is extended or adjusted under 35 U.S.C. 154(b) by 0 days. days.

(21) Appl. No.: 14/999,715

(22) Filed: Jun. 17, 2016

Related U.S. Application Data

(60) Provisional application No. 62/230,932, filed on Jun. 20, 2015.

(51) Int. Cl.
*A61K 36/74* (2006.01)
*A61K 45/06* (2006.01)

(52) U.S. Cl.
CPC .............. *A61K 36/74* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2003/0191191 | A1* | 10/2003 | Blume ................. | A61K 31/137 514/650 |
| 2008/0039463 | A1* | 2/2008 | Nadeson ............ | A61K 31/4355 514/235.5 |
| 2010/0184817 | A1* | 7/2010 | Wolicki ................. | A61K 31/24 514/401 |
| 2011/0086088 | A1* | 4/2011 | Berry ....................... | A61K 8/46 424/450 |

OTHER PUBLICATIONS

The University of Chicago Center for Peripheral Neuropathy, Types of Peripheral Neuropathy-Pre-Diabetic/Diabetic, Apr. 16, 2010.*
Poulaliou A, Itch and pain characteristics in skin carcinomas, acta derm venerol, 96, 2016, 697.*
Ocampo, R. & Balick, M. "Plants of Semillas Sagradas: An Ethnobedicinal Garden in Costa Rica", 2009 Finca Luna Nueva Extractos de Costa Rica, ISBN 978-0-615-27415-7; XP-002658384 , pp. 52, 53.
Pages 144, 145, 417-420, 505 from Scarlet bush, ED—Taylor L., in "The Healing Power of Rainforest Herbs, Squareone"—Jan. 1, 2005 XP009152071.
"Peripheral Neuropathy" Janet M. Torpy, MD from jamanetwork. com website, 6 pages from Mar. 2008. http://jama.jamanetwork.com/article.aspx?articleid=181568.
"Peripheral Neuropathy Fact Sheet" friom NIH website, 18 pages. http://www.ninds.nih.gov/disorders/peripheralneuropathy/detail_peripheralneuropathy.htm.
"Peripheral Neuropathy", Regular review by Richard A C Hughes , BMJ vol. 324, pp. 466-469, Feb. 2002.
Esposito-Avella et al. *"Pharmacological Screening of Panamanian Medicinal Plants, Part I"* J. Crude Drug Res. 23 (1985) No. 1, pp. 17-25.
"New Insights Into Diabetic Polyneuropathy" Michael Polydefkis, MD JAMA 2003, 290(10): 1371-1376.

* cited by examiner

*Primary Examiner* — Celeste A Roney
(74) *Attorney, Agent, or Firm* — Chris Whewell

(57) ABSTRACT

Methods are provided for relieving pain associated with peripheral neuropathy, by topical application to human skin of a topical composition comprising *Hamelia patens* extract in combination with a dermatologically-acceptable carrier. According to methods of the invention, the topical composition is applied to human skin at a sufficient concentration and for a sufficient time to relieve pain associated with peripheral neuropathy.

20 Claims, No Drawings

TREATMENT OF PAIN IN PERIPHERAL NEUROPATHY USING TOPICAL HAMELIA PATENS EXTRACT

CROSS REFERENCE TO RELATED APPLICATIONS

This application claims the benefit of U.S. Provisional Application No. 62/230,932 filed on Jun. 20, 2015, the entire contents of which are hereby incorporated herein by referenec.

TECHNICAL FIELD

This invention relates generally to symptomatic relief of pain. More particularly, it relates to topical compositions comprising an extract of the plant species *Hamelia patens*, and to the use of such compositions in relieving pain associated with the medical conditions known to involve peripheral neuropathy.

BACKGROUND OF THE INVENTION

Various compositions and materials have been proffered in the past as being beneficial for relieving pain in human subjects. The field of analgesia dates back over 2000 years ago, known by archaeological evidence of earlier peoples ingesting opiates. In the modern era, opiates and semi-synthetic opiates are in extensive use, as well as non-opiate pain-relieving medications including non-steroidal anti-inflammatory drugs ("NSAIDS"), salicylic acid derivatives (aspirin) and naturopathic pain remedies. However, with the exception of salves, skin creams, ointments or lotions which include a topical anesthetic such as benzocaine, lidocaine, and camphor, there are currently no effective topical formulations useful for relieving pain.

Peripheral neuropathy is a specifically-named disease condition that affects a significant portion of the patient population, producing chronic pain patterns usually in the extremities of the human body. The pain characteristics of peripheral neuropathy are unique from the diffuse pain patterns of headache, backache, arthritis, arthralgia and rheumatism.

Pain distribution in peripheral neuropathy is related to the distribution of the affected nerve trunk involved. The intensity of the pain is directly related to the degree of intensity of nerve fiber damage. Once a peripheral neuropathy pain pattern is established, the pain pattern becomes a chronic pain that is recurring in nature. Thus, the pain associated with peripheral neuropathy is very specific, and is well-known in the art to be differentiable over other types of pain. Peripheral neuropathy is diagnosed using a standard diagnostic procedure that is unique to peripheral neuropathy, called nerve conduction tests ("NCT"). Nerve conduction tests are physician-directed, in the field of clinical neurology.

Peripheral neuropathy is damage or disease affecting nerves, which may impair sensation, movement, or other aspects of health depending on the type of nerve affected. Common causes include systemic diseases such as diabetes or leprosy, vitamin deficiencies, medications (e.g. systemic chemotherapy given for cancer treatments), traumatic injury, i.e., post-surgical following cancer surgery, excessive alcohol consumption, compression neuropathy secondary to Herniated Nucleus Pulposus, immune system disease sequelae, post-radiation treatments. In some instances, peripheral neuropathy can be inherited from birth.

Peripheral neuropathy can be either acute or chronic, and often occurs with more than one type of nerve tissue affected at the same time in an individual subject patient. Peripheral neuropathy is classified according to the type of nerve involved, or by its underlying cause. For instances in which the cause is unknown, peripheral neuropathy is described as idiopathic neuropathy.

Despite advances in the understanding of the pathophysiology of the metabolic causes of peripheral neuropathy, successful drug treatment of symptoms of peripheral neuropathy has been limited. The only three approaches currently approved by the United States Food and Drug Administration at the time of this writing for treating peripheral neuropathy are systemic drug therapies, involving: 1) tricyclic anti-depressant compounds; 2) anti-epileptic/anti-convulsant drugs; and 3) a long-acting opioid analgesic.

Prior to the present invention, there has been no known effective topical medicament useful for symptomatic relief of pain resulting from peripheral neuropathy, nor has there been any treatment for peripheral neuropathy approved by the United States Food and Drug Administration which is topically applied to the skin.

SUMMARY OF THE INVENTION

Provided are compositions of matter useful for symptomatic relief of pain associated with peripheral neuropathy, which comprise a dermatologically-acceptable carrier in combination with at least one material selected from the group consisting of: pigenin-7-o-beta d-glucuronide; aricine; catequine; 24-methylenecycloartane-3β-ol; 24-methylcycloart-24-en-3β-ol; 2E-3,7,11,15,19-pentamethyl-2-eicosane-1-ol; ephedrine; flavonones; 2'-5-5'-7-tetrahydroxy-7-o-rutinoside; isomaruquine; isopteropodine; maruquine; the methyl ester of maruquine; narirutin; narirutin (2r); narirutin (2s); oxindole alkaloids; oxindole aricine; palmirine; pteropodine; rumberine; rosmarinic acid; rotundic acid; rumberine; rutin; seneciophylline; β-sito sterol; speciophylline; stigmast-4-en-3-3-dione; stigmast-4-en-3-6-di-one; stigmasterol; tannins; and ursolic acid, and including any mixtures of any one or any more than one thereof in any proportion, present in an sufficient quantity in a dermatologically-acceptable carrier to render a composition of the invention to be suitable for use as a topical composition that is useful to be topically applied to human skin for symptomatic relief from pain associated with peripheral neuropathy.

Also provided are methods for providing symptomatic relief from pain associated with peripheral neuropathy in human subjects suffering from or experiencing pain associated with peripheral neuropathy A method according to some embodiments of the invention comprises providing a topical composition containing *Hamelia patens* extract in combination with a dermatologically-acceptable carrier and applying the topical composition to the skin of a human subject sufficiently to provide symptomatic relief from pain associated with peripheral neuropathy.

DETAILED DESCRIPTION

This disclosure concerns the plant known as *Hamelia patens*, its parts, and extracts or extract concentrates prepared therefrom, constituents thereof, and their use in symptomatic relief of pain resulting from or otherwise associated with peripheral neuropathy. *Hamelia patens* is a perennial shrub or shrub-like plant that is sometimes referred to as Scarlet Bush, Firebush, and Texas Firecracker, among other common names. *Hamelia patens* grows in Florida, Texas, and other southern and southwestern states, and is also distributed throughout parts of central and south America. The plant has a woody stem and roots, broad leaves and at maturity produces bright red berries. An extract provided in accordance with this disclosure is produced using any combination of parts of the *Hamelia patens* plant, of any of its sub-species, which parts are selected from the group consisting of: its roots, stems, leaves, and fruit.

A *Hamelia patens* extract in some embodiments according to this disclosure is provided by first picking leaves from a sub-species of the plant, the sub-species in some non-limiting embodiments being *Hamelia patens* jacq. In one exemplary embodiment about 509 grams of freshly-picked leaves of *Hamelia patens* Jacq. were procured from *Hamelia patens* jacq. grown in Texas. Stems were removed from the leaves and the leafy material was cut transversely into strips. The cut leafy material was combined with about 475 milliliters of CETAPHIL@ gentle skin cleanser (Galderma Laboratories) in a covered one-liter beaker and blended using a stirring rod until the leafy material was evenly distributed throughout the bulk of the composition. The contents of the beaker were heated to 65.5 degrees centigrade for 30 minutes with frequent stirring. During the course of the heating the leaves turned to a dull green with a brown cast. At the end of the 30 minutes the leafy material was compacted using a potato masher, to squeeze more of the plant-borne matter from the leaves and into the bulk of the composition. Finally, the beaker's contents were poured through a stainless steel screen, of sufficient mesh to separate the solid matter including leaves from the liquid portion, which liquid portion itself was subsequently strained through cheesecloth, thus providing a liquid *Hamelia patens* extract suitable for topical application to human skin to relieve pain associated with peripheral neuropathy in a human subject. As used herein, "human skin" includes any skin located on any part of the body of a human subject.

In other embodiments useful for providing a *Hamelia patens* extract, a protic solvent such as water, or a lower alcohol (any C1-C4 alcohol), or a mixture comprising a plurality of lower alcohols, or blends comprising one or a plurality of lower alcohols and water, when miscible, in any relative proportions, is employed as a liquid solvent into which the constituents of *Hamelia patens* are extracted from the plant. In some embodiments the lower alcohol is any alcohol selected from any C1-C4 alcohol, including any mixtures thereof, independently selected to be present in any desired proportion. In some embodiments a water/alcohol mixture containing any amount in the range from about 5% to about 10% by volume of the alcohol in water is used as a solvent. Various extraction techniques known in the art may be employed, including percolation, soxhlet extraction, and other extraction techniques, including those employing supercritical carbon dioxide. In one embodiment about 500 grams of dried *Hamelia patens* leaves ground to a coarse powder are combined with about 500 ml of a mixture that is 10% by volume of ethanol and 90% by volume of water, in a suitable vessel and heated to about 65 degrees centigrade for 30 minutes. In alternate embodiments, the solvent is maintained at room temperature and the mixture of plant matter and solvent is permitted to percolate for an extended time, of 24 hours. In other embodiments, a longer extraction time in the range of between about 24 hours and about 72 hours is employed. The resulting solution from such heating, percolation, or other extraction technique is centrifuged (optionally) and filtered to provide a liquid solution *Hamelia patens* extract. This solution extract is in some embodiments applied as-is to human skin to relieve pain associated with peripheral neuropathy. In alternate embodiments various other materials may be combined with such solution extract to form skin creams, lotions, salves, ointments, etc., as described below prior to its application to human skin for relief of pain associated with peripheral neuropathy. In some embodiments, the solvent present in such a liquid solution extract is removed using techniques known to those skilled in the art (including reduced pressure distillation, flash evaporation, nitrogen sweep, etc.) to yield an extract in the form of a dry powder, crystalline, amorphous, or other solid, or semi-solid form. In some embodiments, the temperature of the liquid solvent extract is not permitted to exceed about 50 degrees centigrade during solvent removal. In one embodiment when a solvent comprising 10% by volume ethanol in 90% by volume water is employed at room temperature in a percolation lasting about 24 hours, the yield of dry *Hamelia patens* extract provided following solvent removal amounts to about 7% by weight based on the weight of the fresh-cut *Hamelia patens* leaves employed. Typically by such processing the yield of *Hamelia patens* extract ranges from between about 2% to about 8% by weight based on the weight of the plant matter used. While an extract of the *Hamelia patens* plant is in some embodiments crystalline in nature, it is understood by those skilled in the art that extracts of the plant *Hamelia patens* obtained following solvent removal may not always be perfectly crystalline or powdered crystalline in nature owing to variation among individual plants' growing condition, time of harvest, and genetics, which can impact the quantity of polymeric residues present or other aspects of composition which affect crystallinity. Thus, in some embodiments a non-completely-crystalline residue or extract may be obtained from an extraction of a *Hamelia patens* plant, such as extracts comprised of or which include amorphous or partially-gummy residues or components; however in general such non-completely crystalline extracts obtained are viewed as being equivalent to a crystalline extract for purposes of this disclosure and these forms are all to be treated herein as being included in the term *Hamelia patens* extract where the context does not otherwise exclude non-crystalline or gummy or other residues or components. Thus, the words *Hamelia patens* extract refers to crystalline, non-crystalline, amorphous, and any other physically observable form of the material which results from an extraction of the *Hamelia patens* plant that is free from the solvent that was used to extract it from the plant matter. A *Hamelia patens* extract when specified herein can be the material obtained from *Hamelia patens* when the plant is extracted with either water, or other solvents including aqueous alcoholic solvents, and can be mixtures of extracts obtained using various solvents. In some embodiments the *Hamelia patens* extract is an aqueous extract, i.e., produced as a result of the plant matter being extracted with water. In other embodiments the *Hamelia patens* extract is an aqueous alcohol extract. In some embodiments the *Hamelia patens* extract is mixture of extracts from both aqueous and aqueous alcoholic, or alcoholic extracts in any desired or selected proportion.

Compositions according to some embodiments of the disclosure are prepared by mixing dry powdered *Hamelia patens* extract with various other materials, as desired, such other materials collectively comprising a dermatologically-acceptable carrier. In some embodiments the crystalline *Hamelia patens* extract is ground with a mortar or otherwise pulverized, or liquefied by addition of any selected suitable solvent, and combined with or formulated into a skin crime or skin lotion, salve, etc. at any desired concentration, to provide a medicament suitable for topical application to human skin in which the concentration of *Hamelia patens* extract is pre-selected to be any concentration between about 0.05% by weight and about 85% by weight based on the weight of the final medicament composition, including all weight percentages and ranges of weight percentages therebetween.

In some embodiments a crystalline *Hamelia patens* extract is blended with at least one other material that is a solid or liquid at room temperature, in any suitable or desired amount, in order to provide a *Hamelia patens* extract concentrate that can be used to conveniently provide finished topical medicaments by combination with other materials, as desired. Such at least one other material in some embodiments comprises a material selected from the group consisting of: silicates, aluminosilicates and silica present in effective flow-enhancing amounts to enable the *Hamelia patens* extract to flow freely when poured. In other embodiments, a *Hamelia patens* extract according to the disclosure is combined with a solvent, to provide a solution that comprises a *Hamelia patens* extract concentrate, in which *Hamelia patens* extract is present in any amount between about 1% by weight based on the total weight of the concentrate, up to the saturation limit of the *Hamelia patens* extract in the solvent employed, at ambient temperatures.

In some embodiments a *Hamelia patens* extract is combined with a glyceryl ester based oil that is either plant-derived or animal-derived, and in some embodiments with any pre-selected mixture of glyceryl ester based oils. Suitable exemplary glyceryl ester based oils include without limitation oils such as soybean oil, coconut oil, palm oil, palm kernel oil, corn oil, olive oil, sunflower oil, safflower oil, cottonseed oil, rape oil including Canadian oil low acid, almond oil, sesame oil, peanut oil, beef tallow, lard, emu oil, butterfat, and mixtures thereof in any selected proportion. A composition according to some embodiments of this disclosure includes a *Hamelia patens* extract in combination with a glyceryl ester oil (alternately mixtures including a plurality of such oils, each present in any proportion), wherein the *Hamelia patens* extract is present in any amount between 0.05% by weight to 85% by weight, based on the total weight of the composition, including all percentages by weight and ranges of percentages by weight therebetween. The presence of a fatty acid glyceryl ester oil as a vehicle in general is capable of facilitating or assisting in transdermal passage of one or more component materials present in *Hamelia patens* extract into and through human skin. A glyceryl ester oil can also in some embodiments be used in place of water, alcohol or a mixture of water and alcohol as described herein, as the solvent into which a *Hamelia patens* extract is initially made from the plant material, such glyceryl ester oil solvent being subsequently separated from the constituents of the *Hamelia patens* that were extracted, if desired, using conventional techniques as reduced pressure distillation, molecular distillation, chromatography, etc. Thus, instead of steeping, percolating, etc. *Hamelia patens* plant parts in a solvent of water, alcohol, or an alcohol-water mixture, any glyceryl ester oil including without limitation those listed above, can be employed as a solvent in the extraction process. Following extraction, in some embodiments the glyceryl ester oil that is laden with constituent materials of the *Hamelia patens* plant can be filtered and then used directly as an ingredient in a topical medicament composition according to some embodiments of the present invention.

In other embodiments, a *Hamelia patens* extract is combined with water or a water/alcohol mixture as described above to provide a solubilized form of *Hamelia patens* extract useful to provide topical medicament compositions according to the disclosure.

Compositions according to some embodiments of the disclosure include a *Hamelia patens* extract in combination with water, in alternate embodiments in combination with alcohol, in alternate embodiments in combination with water/alcohol mixtures, in alternate embodiments in combination with glyceryl ester oil(s) as solvent, and in these embodiments the amount of *Hamelia patens* extract (crystalline or otherwise) is present in any desired amount between 0.05% by weight and up to the solubility limit of the solvent selected, which can be as high as 85% by weight of *Hamelia patens* extract, based on the total weight of the composition, including all percentages by weight and ranges of percentages by weight therebetween. In different embodiments any C1 to C4 alcohol (including any mixtures thereof in any proportion) are used, as solvent, either mixed with water in any chosen proportion, or anhydrous or substantially anhydrous. Any vegetable oil or plant-derived glyceryl ester oil may also be used as a solvent for making an extract of *Hamelia patens* using the same techniques as for the use of water, alcohols, or water-alcohol mixtures described herein.

In another exemplary embodiment, about a one-liter volume of cut *Hamelia patens* leaves are compressed and combined with about 125 ml of petrolatum, the mixture being heated to any temperature in the range of between about sixty (60) degrees centigrade and about eighty (80) degrees centigrade for about 10 minutes. This provides a hydrocarbon base containing *Hamelia patens* extract that is in some embodiments applied directly to human skin, or alternately is useful in preparing compositions according to other embodiments of this disclosure comprising other ingredients known to be used or useful in dermatologically-acceptable carriers. In some embodiment this petrolatum-borne extract is combined with effective amounts of one (and alternately any number more than one) of an anti-inflammatory, anti-oxidant, and/or anti-bacterial material to provide an enhanced *Hamelia patens* extract. Such a petrolatum-borne *Hamelia patens* extract is easy to handle enabling quick and ready blending with other materials. In other embodiments, a powdered crystalline *Hamelia patens* extract is combined with petrolatum and heated with agitation to provide a composition according to the disclosure wherein the extract of *Hamelia patens* is present in any amount between 0.05% by weight to 85% by weight, based on the total weight of the petrolatum-based composition, including all percentages by weight and ranges of percentages by weight therebetween.

In another embodiment, a liquid solution *Hamelia patens* extract, (for example prepared by combining *Hamelia patens* plant parts with a solvent and percolating at about 60 degrees centigrade) wherein the solvent is a 90% water/10% ethanol (by volume) mixture is combined with any vegetable oil or any glycerol ester oil to provide a mixture that is heated with stirring sufficiently to simmer off the water and alcohol present, under ambient or reduced pressure, causing the *Hamelia patens* extract to be taken up into the oil. For such embodiments, the quantity of water/ethanol extract and oil used are selected to provide an amount of *Hamelia patens* extract present in the final composition in any amount between 0.05% by weight and 85% by weight, based on the total weight of the composition, including all percentages by weight and ranges of percentages by weight therebetween. In alternate embodiments, one begins with a crystalline *Hamelia patens* extract and dissolves it in water/ethanol mixture comprising about 10% ethanol by volume and once dissolved, this mixture is combined with any desired amount of oil, the water/ethanol present is subsequently removed to afford an oil-borne *Hamelia patens* extract.

Thus, the present disclosure in some embodiments provides compositions comprising a crystalline *Hamelia patens* extract in combination with at least one material selected from the group consisting of: water, water/alcohol mixtures, hydrocarbons (petrolatum) and ester-type fats or oils, wherein the *Hamelia patens* extract is present in any amount between 0.05% by weight to 85% by weight, based on the total weight of the composition, including all percentages by weight and ranges of percentages by weight therebetween.

Crystalline or liquid (including aqueous, non-aqueous, alcoholic, hydrocarbon-based, and oil-borne) *Hamelia patens* extracts as provided herein may be further refined to isolate or concentrate any one, or more than one, of the compounds present in *Hamelia patens* using methods or techniques generally known to those skilled in the art including without limitation solvent extraction based on acid/base properties of the constituents, distillation, steam distillation, molecular distillation, and chromatography.

A *Hamelia patens* extract provided according to some embodiments of the disclosure contains at least any one compound, and in other embodiments contains any mixture comprising a plurality including any two or more than two of the following compounds: alkaloids, 2-alpha-hydroxyursolic acid, apigenin-7-o-beta d-glucuronide, aricine, catequine, 19-alphahydroxy Asiatic acid, 24-methylenecycloartane-3β-ol, 24-methylcycloart-24-en-3β-ol, 2E-3,7,11,15,19-pentamethyl-2-eicosane-1-ol, ephedrine, flavonones, 2'-5-5'-7-tetrahydroxy-7-o-rutinoside, isomaruquine, isopteropodine, maruquine, the methyl ester of maruquine, mitraphylline, narirutin, narirutin (2r), narirutin (2s), oxindole alkaloids, oxindole aricine, palmirine, pigenin-7-o-beta D-glucuronide, pomolic acid, pteropodine, rumberine, rosmarinic acid, rotundic acid, rumberine, rutin, seneciophylline, 8-sito sterol, speciophylline, stigmast-4-en-3-3-dione, stigmast-4-en-3-6-dione, stigmasterol, tannins, tormentic acid, uncarine F, and ursolic acid. In some embodiments, all of these compounds are present in a *Hamelia patens* extract useful for symptomatic relief from pain associated with peripheral neuropathy.

Accordingly, a *Hamelia patens* extract as provided in some embodiments contains alkaloids. In some embodiments alkaloids are present in a composition useful according to the disclosure in any amount between about 0.05% and about 30% by weight based on the total weight of the composition, including all weight percents and ranges of weight percents therebetween. A *Hamelia patens* extract as provided in some embodiments contains apigenin-7-o-beta d-glucuronide. In some embodiments apigenin-7-o-beta d-glucuronide is present in a composition useful according to the disclosure in any amount between about 0.05% and about 30% by weight based on the total weight of the composition, including all weight percents and ranges of weight percents therebetween. A *Hamelia patens* extract as provided in some embodiments contains aricine. In some embodiments aricene is present in a composition useful according to the disclosure in any amount between about 0.05% and about 30% by weight based on the total weight of the composition, including all weight percents and ranges of weight percents therebetween. A *Hamelia patens* extract as provided in some embodiments contains catequine. In some embodiments catequine is present in a composition useful according to the disclosure in any amount between about 0.05% and about 30% by weight based on the total weight of the composition, including all weight percents and ranges of weight percents therebetween. A *Hamelia patens* extract as provided in some embodiments contains 24-methylenecycloartane-3β-ol. In some embodiments 24-methylenecycloartane-3β-ol is present in a composition useful according to the disclosure in any amount between about 0.05% and about 30% by weight based on the total weight of the composition, including all weight percents and ranges of weight percents therebetween. A *Hamelia patens* extract as provided in some embodiments contains 24-methylcycloart-24-en-3β-ol. In some embodiments 24-methylcycloart-24-en-3β-ol is present in a composition useful according to the disclosure in any amount between about 0.05% and about 30% by weight based on the total weight of the composition, including all weight percents and ranges of weight percents therebetween. A *Hamelia patens* extract as provided in some embodiments contains 2E-3,7,11,15,19-pentamethyl-2-eicosane-1-ol. In some embodiments 2E-3,7,11,15,19-pentamethyl-2-eicosane-1-ol is present in a composition useful according to the disclosure in any amount between about 0.05% and about 30% by weight based on the total weight of the composition, including all weight percents and ranges of weight percents therebetween. A *Hamelia patens* extract as provided in some embodiments contains ephedrine. In some embodiments ephedrine is present in a composition useful according to the disclosure in any amount between about 0.05% and about 30% by weight based on the total weight of the composition, including all weight percents and ranges of weight percents therebetween. A *Hamelia patens* extract as provided in some embodiments contains flavonones. In some embodiments flavonones are present in a composition useful according to the disclosure in any amount between about 0.05% and about 30% by weight based on the total weight of the composition, including all weight percents and ranges of weight percents therebetween. A *Hamelia patens* extract as provided in some embodiments contains 2'-5-5'-7-tetrahydroxy-7-o-rutinoside. In some embodiments 2'-5-5'-7-tetrahydroxy-7-o-rutinoside is present in a composition useful according to the disclosure in any amount between about 0.05% and about 30% by weight based on the total weight of the composition, including all weight percents and ranges of weight percents therebetween. A *Hamelia patens* extract as provided in some embodiments contains 19-alpha-hydroxy asiatic acid. In some embodiments 19-alpha-hydroxy asiatic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains isomaruquine. In some embodiments isomaruquine is present in a composition useful according to the disclosure in any amount between about 0.05% and about 30% by weight based on the total weight of the composition, including all weight percents and ranges of weight percents therebetween. A *Hamelia patens* extract as provided in some embodiments contains isopteropodine. In some embodiments isopteropodine is present in a composition useful according to the disclosure in any amount between about 0.05% and about 30% by weight based on the total weight of the composition, including all weight percents and ranges of weight percents therebetween. A *Hamelia patens* extract as provided in some embodiments contains maruquine. In some embodiments maruquine is present in a composition useful according to the disclosure in any amount between about 0.05% and about 30% by weight based on the total weight of the composition, including all weight percents and ranges of weight percents therebetween. A *Hamelia patens* extract as provided in some embodiments contains the methyl ester of maruquine. In some embodiments the methyl ester of maruquine is present in a composition useful according to the disclosure in any amount between about 0.05% and about 30% by weight based on the total weight of the composition, including all weight percents and ranges of weight percents therebetween. A *Hamelia patens* extract as provided in some embodiments contains mitraphylline. In some embodiments mitraphylline is present in a composition useful according to the disclosure in any amount between about 0.05% and about 30% by weight based on the total weight of the composition, including all weight percents and ranges of weight percents therebetween. A *Hamelia patens* extract as provided in some embodiments contains narirutin. In some embodiments narirutin is present in a composition useful according to the disclosure in any amount between about 0.05% and about 30% by weight based on the total weight of the composition, including all weight percents and ranges of weight percents therebetween. A *Hamelia patens* extract as provided in some embodiments contains narirutin (2r). In some embodiments narirutin (2r) is present in a composition useful according to the disclosure in any amount between about 0.05% and about 30% by weight based on the total weight of the composition, including all weight percents and ranges of weight percents therebetween. A *Hamelia patens* extract as provided in some embodiments contains narirutin (2s). In some embodiments narirutin (2s) is present in a composition useful according to the disclosure in any amount between about 0.05% and about 30% by weight based on the total weight of the composition, including all weight percents and ranges of weight percents therebetween. A *Hamelia patens* extract as provided in some embodiments contains oxindole alkaloids. In some embodiments oxindole alkaloids are present in a composition useful according to the disclosure in any amount between about 0.05% and about 30% by weight based on the total weight of the composition, including all weight percents and ranges of weight percents therebetween. A *Hamelia patens* extract as provided in some embodiments contains oxindole In some embodiments oxindole aricine is present in a composition useful according to the disclosure in any amount between about 0.05% and about 30% by weight based on the total weight of the composition, including all weight percents and ranges of weight percents therebetween. A *Hamelia patens* extract as provided in some embodiments contains palmirine. In some embodiments palmirine is present in a composition useful according to the disclosure in any amount between about 0.05% and about 30% by weight based on the total weight of the composition, including all weight percents and ranges of weight percents therebetween. A *Hamelia patens* extract as provided in some embodiments contains pigenin-7-o-beta D-glucuronide. In some embodiments pigenin-7-o-beta D-glucuronide is present in a composition useful according to the disclosure in any amount between about 0.05% and about 30% by weight based on the total weight of the composition, including all weight percents and ranges of weight percents therebetween. A *Hamelia patens* extract as provided in some embodiments contains pomolic acid. In some embodiments pomolic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains pteropodine. In some embodiments pteropodine is present in a composition useful according to the disclosure in any amount between about 0.05% and about 30% by weight based on the total weight of the composition, including all weight percents and ranges of weight percents therebetween. A *Hamelia patens* extract as provided in some embodiments contains rumberine. In some embodiments rumberine is present in a composition useful according to the disclosure in any amount between about 0.05% and about 30% by weight based on the total weight of the composition, including all weight percents and ranges of weight percents therebetween. A *Hamelia patens* extract as provided in some embodiments contains rosmarinic acid. In some embodiments rosmarinic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains rotundic acid. In some embodiments rotundic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains rumberine. In some embodiments rumberine is present in a composition useful according to the disclosure in any amount between about 0.05% and about 30% by weight based on the total weight of the composition, including all weight percents and ranges of weight percents therebetween. A *Hamelia patens* extract as provided in some embodiments contains rutin. In some embodiments rutin is present in a composition useful according to the disclosure in any amount between about 0.05% and about 30% by weight based on the total weight of the composition, including all weight percents and ranges of weight percents therebetween. A *Hamelia patens* extract as provided in some embodiments contains seneciophylline. In some embodiments seneciophylline is present in a composition useful according to the disclosure in any amount between about 0.05% and about 30% by weight based on the total weight of the composition, including all weight percents and ranges of weight percents therebetween. A *Hamelia patens* extract as provided in some embodiments contains β-sit osterol. In some embodiments β-sitosterol is present in a composition useful according to the disclosure in any amount between about 0.05% and about 30% by weight based on the total weight of the composition, including all weight percents and ranges of weight percents therebetween. A *Hamelia patens* extract as provided in some embodiments contains speciophylline. In some embodiments speciophylline is present in a composition useful according to the disclosure in any amount between about 0.05% and about 30% by weight based on the total weight of the composition, including all weight percents and ranges of weight percents therebetween. A *Hamelia patens* extract as provided in some embodiments contains stigmast-4-en-3-3-dione. In some embodiments stigmast-4-en-3-3-dione is present in a composition useful according to the disclosure in any amount between about 0.05% and about 30% by weight based on the total weight of the composition, including all weight percents and ranges of weight percents therebetween. A *Hamelia patens* extract as provided in some embodiments contains stigmast-4-en-3-6-dione. In some embodiments stigmast-4-en-3-6-dione is present in a composition useful according to the disclosure in any amount between about 0.05% and about 30% by weight based on the total weight of the composition, including all weight percents and ranges of weight percents therebetween. A *Hamelia patens* extract as provided in some embodiments contains stigmasterol. In some embodiments stigmasterol is present in a composition useful according to the disclosure in any amount between about 0.05% and about 30% by weight based on the total weight of the composition, including all weight percents and ranges of weight percents therebetween. A *Hamelia patens* extract as provided in some embodiments contains tannins. In some embodiments tannins are present in a composition useful according to the disclosure in any amount between about 0.05% and about 30% by weight based on the total weight of the composition, including all weight percents and ranges of weight percents therebetween. A *Hamelia patens* extract as provided in some embodiments contains tormentic acid. In some embodiments tormentic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains uncarine F. In some embodiments uncarine F is present in a composition useful according to the disclosure in any amount between about 0.05% and about 30% by weight based on the total weight of the composition, including all weight percents and ranges of weight percents therebetween. A *Hamelia patens* extract as provided in some embodiments contains ursolic acid. In some embodiments ursolic acid is present in a composition useful according to the disclosure in any amount between about 0.05% and about 30% by weight based on the total weight of the composition, including all weight percents and ranges of weight percents therebetween. A *Hamelia patens* extract as provided in some embodiments contains 2-alpha-hydroxy ursolic acid. In some embodiments 2-alpha-hydroxy ursolic acid is present in a composition useful according to the disclosure in any amount between about 0.05% and about 30% by weight based on the total weight of the composition, including all weight percents and ranges of weight percents therebetween. The term "about" when used herein, such as in "about 30%", is to be understood as also including the exact numerical value occurring immediately subsequent to the word "about", in the same context. For example, the recitation of "about 30%" and "about 0.05%" includes the exact value specified, in this instance exactly 30% and exactly 0.05%, respectively. In some embodiments, each of the component materials in the listing above, when present in a *Hamelia patens* extract, are present in amounts within the above-specified ranges independently with respect to the amounts of the other component materials present.

As concerns any one or more than one of the foregoing materials in said listing which are described as being acids, the present disclosure includes the presence of such materials in their neutralized or anionic forms, and in alternate embodiments their esterified forms condensed with any alcohol or polyol selected. For those component compounds in the listing having a carboxylic acid function, the present disclosure includes the presence of such materials in their anionic forms, including without limitation their alkali metal salts, alkaline earth salts, ammonium salts and substituted ammonium salts, the concentration of the anionic forms of such material(s) being present in a composition according to the disclosure in the amounts specified for the acid form of the material(s). In some embodiments the concentration ranges for components present in a composition according to the disclosure are applied based on the weight percent of the anionic form of the material. In some embodiments, the concentration ranges in a composition according to the disclosure are determined based on the weight percent of the salt, including the cation present. Likewise when basic substances are recited, the present disclosure includes the presence of such materials in their protonated forms, the concentration ranges of such materials being present in a composition according to the disclosure in the amounts specified above for the basic form. In some embodiments the concentration ranges for a composition according to the disclosure is determined based on the weight percent of the protonated form of the material present. In some embodiments, the concentration ranges for a composition according to the disclosure is determined based on the weight percent of the protonated form of the material and including its anion present for charge neutrality.

In some embodiments, all of the materials in the above listing are present in a composition useful according to the disclosure. In other embodiments any one or more than one of the materials in the above listing are independently omitted from the contents of a composition useful according to the disclosure, such as by refining a *Hamelia patens* extract (including a crystalline *Hamelia patens* extract) for the purpose of removal of one, or any number greater than one, of component materials in the above listing present in the extract using techniques known to those skilled in the art. In other embodiments any one or any number greater than one of such components present in the listing may be purified using techniques known to those of ordinary skill in the art. For example, to remove nitrogenous bases the extract material is put up into aqueous solution and made alkaline, and extraction done using $CHCl_3$ to remove amino compounds, the aqueous layer being subsequently re-acidified or neutralized. In some embodiments, ammonia is used to make the material alkaline for purposes of such extraction, which ammonia is subsequently removed after the extraction having been completed by blowing with nitrogen or distilling or heating under reduced pressure. In other embodiments an aqueous extract of *Hamelia patens* is made slightly acidic by addition of HCl, and extractions are done using ethyl acetate, ether, chloroform, and/or hexanes. Following extraction, the aqueous layer is subjected to reduced pressure and slight heating or a sweep of nitrogen or other inert gas to facilitate removal of the HCl. In such embodiments, fractions obtained may be further treated to selectively separate or remove component materials present, using techniques known in the art including without limitation such techniques as preparatory chromatography columns, fractional distillation under vacuo, molecular distillation, precipitation and filtration, etc. In further embodiments, any one or more than one of any of the above-named components in the listing are produced synthetically or are otherwise acquired or produced, and are subsequently blended with one another to provide a blend that comprises a synthetic *Hamelia patens* extract that is useful according to the disclosure, such components that are selected to be present each being individually present at levels within the ranges specified herein based on the total weight of the topical medicament produced using *Hamelia patens* extract.

An extract of the plant *Hamelia patens* according to some embodiments of the disclosure may thus comprise a crude (water-based, H2O/alcohol based, oil-based, or petrolatum based) *Hamelia patens* extract from which any one, or any combination including any number more than one of, the component materials set forth in the listing above are omitted or removed from said extract, the resulting extract being useful according to this disclosure. In some embodiments at least any chosen two of the component materials selected from the group consisting of the materials recited in the listing above remain or are present in a *Hamelia patens* extract useful according to this disclosure, the component materials being independently present at concentrations within any of the ranges specified above in such compositions or extracts. In some embodiments at least any chosen three of the component materials selected from the group consisting of the materials recited in the listing above remain or are present in a *Hamelia patens* extract useful for providing a composition useful according to this disclosure, the component materials being independently present at concentrations within the ranges specified above in such compositions or extracts. In some embodiments at least any chosen four of the component materials selected from the group consisting of the materials recited in the listing above remain or are present in a *Hamelia patens* extract useful according to this disclosure, the component materials being independently present at concentrations within the ranges specified above in such composition or extracts. In some embodiments at least any chosen five of the component materials selected from the group consisting of the materials recited in the listing above remain or are present in a *Hamelia patens* extract useful according to this disclosure, the component materials being independently present at concentrations within the ranges specified above in such compositions or extracts.

This disclosure includes the use of *Hamelia patens* extracts from which some of the components in the listing above have been removed, and also *Hamelia patens* extracts comprising a plurality of the materials in the listing above which are produced by combining previously-isolated purified component materials from such listing. In some embodiments, all alkaloids are omitted or removed when providing a *Hamelia patens* extract useful according to the disclosure, the remaining components of the listing remaining present. In some embodiments, all 2-alpha-hydroxyursolic acid is omitted or removed when providing a *Hamelia patens* extract useful according to the disclosure, the remaining components of the listing remaining present. In some embodiments, all flavonones are omitted or removed when providing a *Hamelia patens* extract according to the disclosure, the remaining components of the listing remaining present. In some embodiments, all apigenin-7-o-beta d-glucuronide is omitted or removed when providing a *Hamelia patens* extract useful according to the disclosure, the remaining components of the listing remaining present. In some embodiments, all aricine is omitted or removed when providing a *Hamelia patens* extract useful according to the disclosure, the remaining components of the listing remaining present. In some embodiments, all catequine is omitted or removed when providing a *Hamelia patens* extract useful according to the disclosure, the remaining components of the listing remaining present. In some embodiments, all flavonones is omitted or removed when providing a *Hamelia patens* extract useful according to the disclosure, the remaining components of the listing remaining present. In some embodiments, all 19-alphahydroxy Asiatic acid is omitted or removed when providing a *Hamelia patens* extract useful according to the disclosure, the remaining components of the listing remaining present. In some embodiments, all 24-methylenecycloartane-3β-ol is omitted or removed when providing a *Hamelia patens* extract useful according to the disclosure, the remaining components of the listing remaining present. In some embodiments, all 24-methylcycloart-24-en-3β-ol is omitted or removed when providing a *Hamelia patens* extract useful according to the disclosure, the remaining components of the listing remaining present. In some embodiments, all 2E-3,7,11,15,19-pentamethyl-2-cicosane-1-ol is omitted or removed when providing a *Hamelia patens* extract useful according to the disclosure, the remaining components of the listing remaining present. In some embodiments, all ephedrine is omitted or removed when providing a *Hamelia patens* extract useful according to the disclosure, the remaining components of the listing remaining present. In some embodiments, all 2'-5-5'-7-tetrahydroxy-7-o-rutinoside is omitted or removed when providing a *Hamelia patens* extract useful according to the disclosure, the remaining components of the listing remaining present. In some embodiments, all flavonones are omitted or removed when providing a *Hamelia patens* extract useful according to the disclosure, the remaining components of the listing remaining present. In some embodiments, all isomaruquine is omitted or removed when providing a *Hamelia patens* extract useful according to the disclosure, the remaining components of the listing remaining present. In some embodiments, all isopteropodine is omitted or removed when providing a *Hamelia patens* extract useful according to the disclosure, the remaining components of the listing remaining present. In some embodiments, all maruquine is omitted or removed when providing a *Hamelia patens* extract useful according to the disclosure, the remaining components of the listing remaining present. In some embodiments, all the methyl ester of maruquine is omitted or removed when providing a *Hamelia patens* extract useful according to the disclosure, the remaining components of the listing remaining present. In some embodiments, all mitraphylline is omitted or removed when providing a *Hamelia patens* extract according to the disclosure, the remaining components of the listing remaining present. In some embodiments, all narirutin is omitted or removed when providing a *Hamelia patens* extract useful according to the disclosure, the remaining components of the listing remaining present. In some embodiments, all narirutin (2r) is omitted or removed when providing a *Hamelia patens* extract useful according to the disclosure, the remaining components of the listing remaining present. In some embodiments, all narirutin (2s) is omitted or removed when providing a *Hamelia patens* extract useful according to the disclosure, the remaining components of the listing remaining present. In some embodiments, all oxindole alkaloids are omitted or removed when providing a *Hamelia patens* extract useful according to the disclosure, the remaining components of the listing remaining present. In some embodiments, all oxindole aricine is omitted or removed when providing a *Hamelia patens* extract useful according to the disclosure, the remaining components of the listing remaining present. In some embodiments, all palmirine is omitted or removed when providing a *Hamelia patens* extract useful according to the disclosure, the remaining components of the listing remaining present. In some embodiments, all pigenin-7-o-beta D-glucuronide is omitted or removed when providing a *Hamelia patens* extract useful according to the disclosure, the remaining components of the listing remaining present. In some embodiments, all pomolic acid is omitted or removed when providing a *Hamelia patens* extract useful according to the disclosure, the remaining components of the listing remaining present. In some embodiments, all pteropodine is omitted or removed when providing a *Hamelia patens* extract useful according to the disclosure, the remaining components of the listing remaining present. In some embodiments, all rumberine is omitted or removed when providing a *Hamelia patens* extract useful according to the disclosure, the remaining components of the listing remaining present. In some embodiments, all rosmarinic acid is omitted or removed when providing a *Hamelia patens* extract useful according to the disclosure, the remaining components of the listing remaining present. In some embodiments, all rotundic acid is omitted or removed when providing a *Hamelia patens* extract useful according to the disclosure, the remaining components of the listing remaining present. In some embodiments, all rutin is omitted or removed when providing a *Hamelia patens* extract useful according to the disclosure, the remaining components of the listing remaining present. In some embodiments, all seneciophylline is omitted or removed when providing a *Hamelia patens* extract useful according to the disclosure, the remaining components of the listing remaining present. In some embodiments, all β-sitosterol is omitted or removed when providing a *Hamelia patens* extract useful according to the disclosure, the remaining components of the listing remaining present. In some embodiments, all speciophylline is omitted or removed when providing a *Hamelia patens* extract useful according to the disclosure, the remaining components of the listing remaining present. In some embodiments, all stigmast-4-en-3-3-dione is omitted or removed when providing a *Hamelia patens* extract useful according to the disclosure, the remaining components of the listing remaining present. In some embodiments, all stigmast-4-en-3-6-dione is omitted or removed when providing a *Hamelia patens* extract useful according to the disclosure, the remaining components of the listing remaining present. In some embodiments, all stigmasterol is omitted or removed when providing a *Hamelia patens* extract useful according to the disclosure, the remaining components of the listing remaining present. In some embodiments, all tannins are omitted or removed when providing a *Hamelia patens* extract useful according to the disclosure, the remaining components of the listing remaining present. In some embodiments, all tormentic acid is omitted or removed when providing a *Hamelia patens* extract useful according to the disclosure, the remaining components of the listing remaining present. In some embodiments, all uncarine F is omitted or removed when providing a *Hamelia patens* extract useful according to the disclosure, the remaining components of the listing remaining present. In some embodiments, all ursolic acid is omitted or removed when providing a *Hamelia patens* extract useful according to the disclosure, the remaining components of the listing remaining present. As a non-limiting example, in some embodiments, all flavones, all rutin, and ephedrine are removed or omitted, the remaining components of the listing remaining present in a *Hamelia patens* extract useful according to this disclosure; however, any one or combination including more than one material in the listing may be removed or omitted. A combination, including a *Hamelia patens* extract, according to the disclosure and useful in accordance with providing compositions according to some embodiments of this disclosure may thus contain any number between about one and about all of the foregoing materials in the listing, in any combination, each, when present, being independently present in any amount within the ranges specified above.

For some embodiments of the disclosure in which it is intended that a *Hamelia patens* extract be contacted with human skin, the extract is present in combination with other materials, of which petrolatum is one non-limiting example. In some embodiments a *Hamelia patens* extract (including those described above which omit one or more than one materials from said listing) is present as a component of a mixture comprising a dermatologically-acceptable carrier, which in some embodiments comprises a lotion, skin crème, ointment, or salve. For these embodiments, "dermatologically-acceptable carrier" is used in its ordinary sense relative to the different embodiments herein, generally including dermatologically-acceptable, non-toxic diluents or vehicles useful in formulation of dermatological compositions for topical application to human skin.

Dermatologically-acceptable carriers can include, without limitation, one or more than one materials selected from the group consisting of buffering agents, solubilizing agents, stabilizing agents, liquids such as water, saline solution, glycerol and ethanol. Such carriers enable a dermatologically-acceptable composition to be formulated as liquids, gels, syrups, slurries, suspensions, emulsions, salves, crèmes, ointments and the like for topical application to human skin to relieve pain associated with peripheral neuropathy. A discussion of analogous pharmaceutically-acceptable carriers is available in Remington's Pharmaceutical Sciences (Mack Pub. Co., N.J. 1991), the general idea being the same insomuch as the topical medicament composition that is to be topically applied to human skin according to this disclosure does not cause any deleterious effects to the subject's skin and acts as a carrier for the *Hamelia patens* extract it contains.

Dermatologically-acceptable carriers include any and all compositions capable of functioning as carriers for *Hamelia patens* extract intended for topical application to human epidermal tissue ("skin") for symptomatic relief from pain associated with peripheral neuropathy, without undue toxicity, incompatibility, instability, allergic response, etc. Numerous examples of ingredients useful in providing dermatologically-acceptable carriers and compositions having dermatologically-acceptable carriers for delivering active agents to the skin are well-known in the art and include without limitation those disclosed in U.S. Pat. Nos. 5,709,868; 4,992,478; 4,820,508; 4,608,392; and 4,559,157, which are incorporated herein by reference thereto. Topical application and words of similar import used herein mean to apply or spread a composition onto the surface of skin. A topical medicament is a composition that is formulated to be administered to skin by topical application. Within the class of dermatologically-acceptable carriers are included water, water-based carriers, alcohols, alcohol-based carriers, oils, and oil-based carriers, mineral oil and petrolatum-based carriers chosen for their ability to dissolve or disperse components present in the *Hamelia patens* extract.

As used herein, "topical composition" means any composition containing an extract of *Hamelia patens* in combination with a dermatologically-acceptable carrier and any other optionally added ingredients known to be used or useful in compositions intended and suitable for application to human skin with no adverse skin reactions occurring. Topical compositions useful in carrying out a method of this invention can include various materials, including moisturizers, anti-oxidants, humectants, defoliants, oils, waxes, emulsions, emulsifiers, chelating agents, buffering agents, preservatives, and various cosmetics. Those of ordinary skill in this art readily recognize there are a myriad of materials that are recognized by those skilled in this art which fall within the above classes.

Topical application of *Hamelia patens* extract is accomplished in some embodiments by providing a combination of *Hamelia patens* extract with a dermatologically-acceptable carrier in which compounds present in the *Hamelia patens* extract are soluble per se, or are effectively solubilized (e.g., as a solution, suspension, emulsion, or microemulsion), and contacting or applying such combinations to human skin.

In some embodiments, relatively low concentrations of *Hamelia patens* extract or any of its selected components in a combination according to the disclosure may be employed for instances in which more frequent topical application to human skin is undertaken, as compared to the frequency of application to human skin of a composition according to the disclosure in which the *Hamelia patens* extract is present at a higher concentrations. In some embodiments a topical medicament composition comprising *Hamelia patens* extract in combination with a dermatologically-acceptable carrier is formulated to contain at least about 0.25% and up to about 25% by weight based on the total weight of the composition of *Hamelia patens* extract, and accordingly suitable carriers can be readily chosen which can solubilize or disperse the components of the *Hamelia patens* extract at such concentrations. In some embodiments, *Hamelia patens* extract is present in a topical composition according to the disclosure in any amount between about 0.01% to about 30% by weight based on the total weight of the topical composition, including all percentages and ranges of percentages therebetween. In some embodiments a topical composition according to the disclosure contains about 10% by weight total *Hamelia patens* extract.

While the carrier for extract of *Hamelia patens* can consist of or comprise a relatively simple solvent or dispersant such as oils, the carrier may comprise materials which aid in percutaneous delivery and penetration of one or more than one of the components of a *Hamelia patens* extract into dermal lipid layers. Many of such compositions are well-known in the art of transdermal drug administration, and can take the form of lotions, creams, ointments, salves, gels and solid compositions (e.g., stick-form preparations). Some typical compositions include lotions containing water and/or alcohols and emollients such as hydrocarbon oils and waxes, silicone oils, hyaluronic acid, vegetable, animal, marine, or marine animal fats or oils, glyceride derivatives, fatty acids or fatty acid esters or alcohols or alcohol ethers, lanolin and derivatives, polyhydric alcohols or esters, wax esters, sterols, phospholipids and other materials having like function, and also emulsifiers (nonionic, cationic or anionic), although some of the emollients inherently possess emulsifying properties. These same general ingredients can be formulated into a crème, a lotion, gels, or solid sticks by utilization of different proportions of the ingredients and/or by inclusion of thickening agents such as gums or other forms of hydrophilic particles or colloids. Such compositions are within the class of those comprising dermatologically-acceptable carriers. In some embodiments those most preferred for topical application to human skin are carriers which are fat-soluble, i.e., those which can penetrate human dermal layers and deliver components of *Hamelia patens* extract to the lipid-rich layers of the skin for relief of pain associated with peripheral neuropathy. In alternate embodiments, a *Hamelia patens* extract according to the disclosure may be applied to human skin using a time-release patch, as are used in hormone delivery, nicotine patches, anti-acne patches, and the like. Crèmes, aqueous solutions, pastes, powders, etc. are all suitable delivery vehicles for an extract of *Hamelia patens* or one or more of its components to human skin.

Thus, a *Hamelia patens* extract of the present disclosure (which term includes crystalline and other extracts mentioned herein, synthetically-assembled or otherwise provided), and alternately any of its components in any number, combination, and quantity as earlier set forth may be present in a wide range of compositions suitable to be applied to human skin. In addition, a *Hamelia patens* extract according to the present disclosure may be present in combination with surfactants and materials which are conventionally recognized as being used in skin care products, in which the concentration of *Hamelia patens* extract ranges from about 1% to up to about 60% by weight based on the total weight of the composition, including all percentages and ranges of percentages therebetween.

Surfactants and other materials which can be used in combination with a *Hamelia patens* extract in forming topical compositions useful for symptomatic relief of pain associated with peripheral neuropathy include without limitation: amphoteric/zwitterionic surfactants; anionic surfactants; nonionic surfactants; cationic surfactants; and optional ingredients, including without limitation those described below.

Amphoteric surfactants suitable for inclusion in a topical composition according to this disclosure comprising a *Hamelia patens* extract or any one or more than one of its components independently present in any amount within the ranges specified above can broadly be described as surface active agents containing at least one anionic and one cationic group and can act as either acids or bases depending on pH. Some of these compounds are aliphatic derivatives of heterocyclic secondary and tertiary amines in which the aliphatic radical may be straight or branched and wherein one of the aliphatic substituents contains from about 6 to about 20, preferably 8 to 18, carbon atoms and at least one contains an anionic water-solubilizing group, e.g., carboxy, phosphonate, phosphate, sulfonate, sulfate.

Zwitterionic surfactants suitable for inclusion in a composition according to this disclosure comprising a *Hamelia patens* extract or any of its components independently present in any amount specified in the ranges above can be described as surface active agents having a positive and negative charge in the same molecule which molecule is zwitterionic at all pH's. Zwitterionic surfactants are exemplified by betaines and sultaines. The zwitterionic compounds generally contain a quaternary ammonium, quaternary phosphonium or a tertiary sulfonium moiety. The cationic atom in the quaternary compound can be part of a heterocyclic ring. In all of these compounds there is at least one aliphatic group, straight chain or branched, containing from about 6 to 20, preferably 8 to 18, carbon atoms and at least one aliphatic substituent containing an anionic water-solubilizing group, e.g., carboxy, sulfonate, sulfate, phosphate or phosphonate.

Examples of amphoteric and zwitterionic surfactants suitable for inclusion in a composition comprising a *Hamelia patens* extract or any of its components independently in any amount specified within the ranges above according to the present disclosure include the alkali metal, alkaline earth metal, ammonium or substituted ammonium salts of alkyl amphocarboxyglycinates and alkylamphocarboxypropionates, alkyl amphodipropionates, alkyl monoacetate, alkyl diacetates, alkylamphoglycinates, and alkyl amphopropionates wherein alkyl represents an alkyl group having from 6 to about 20 carbon atoms. Other suitable surfactants include alkyliminomonoacetates, alkyliminidiacetates, alkyliminopropionates, alkyliminidipropionates, and alkylamphopropylsulfonates having between 12 and 18 carbon atoms, alkyl betaines and alkylamidoalkylene betaines and alkyl sultaines and alkylamidoalkylenehydroxy sulfonates.

Anionic surfactants suitable for inclusion in a composition comprising a *Hamelia patens* extract or any of its components independently present in any amount specified in the ranges above according to the present disclosure art: hose surfactant compounds which contain a long chain hydrocarbon hydrophobic group in their molecular structure and a hydrophilic group, including salts such as carboxylate, sulfonate, sulfate or phosphate groups. The salts may be sodium, potassium, calcium, magnesium, barium, iron, ammonium and amine salts of such surfactants. Anionic surfactants include the alkali metal, ammonium and alkanol ammonium salts of organic sulfuric reaction products having in their molecular structure an alkyl, or alkaryl group containing from 8 to 22 carbon atoms and a sulfonic or sulfuric acid ester group. Examples of such anionic surfactants include water-soluble salts of alkyl benzene sulfonates having between 8 and 22 carbon atoms in the alkyl group, alkyl ether sulfates having between 8 and 22 carbon atoms in the alkyl group and 2 to 9 moles ethylene oxide in the ether group. Other anionic surfactants include alkylsulfosuccinates, alkyl ethersulfosuccinates, olefin sulfonates, alkyl sarcosinates, alkyl monoglyceride sulfates and ether sulfates, alkyl ether carboxylates, paraffinic sulfonates, mono and di-alkyl phosphate esters and ethoxylated derivatives, acyl methyl taurates, fatty acid soaps, collagen hydrosylate derivatives, sulfoacetates, acyl lactates, aryloxide disulfonates, sulfosucinamides, naphthalene-formaldehyde condensates and the like. Aryl groups generally include one and two rings, alkyl generally includes from 8 to 22 carbon atoms and the ether groups generally range from 1 to 9 moles of ethylene oxide (EO) and/or propylene oxide (PO), preferably EO. Specific anionic surfactants which may be selected include linear alkyl benzene sulfonates, including without limitation those such as decylbenzene sulfonate, undecylbenzene sulfonate, dodecylbenzene sulfonate, tridecylbenzene sulfonate, nonylbenzene sulfate and the sodium, potassium, ammonium, triethanol ammonium and isopropyl ammonium salts thereof.

Nonionic surfactants may also be present in a composition according to the disclosure comprising a *Hamelia patens* extract or any of its components independently present in any amount specified within the ranges above. The nonionic surfactant(s) may be any of the known nonionic surfactants which, as with other surfactants discussed herein, are generally selected on the basis of compatibility, effectiveness, and economy, and present in a composition according to the disclosure in effective amount to enhance wettability or permeability of human skin when optically applied thereto or to otherwise beneficially modify activity of components present in a combination provided herein. Examples of useful nonionic surfactants include without limitation condensates of ethylene oxide with a hydrophobic moiety which has an average hydrophilic lipolytic balance (HLB) between about 8 to about 16, and in some embodiments between about 10 and about 13. Non-ionic surfactants include the ethoxylated primary or secondary aliphatic alcohols having from about 8 to about 24 carbon atoms, in either straight or branch chain configuration, with from about 2 to about 40, and in some embodiments between about 2 and about 9 moles of ethylene oxide per mole of alcohol. Other suitable nonionic surfactants include the condensation products of from about 6 to about 12 carbon atoms alkyl phenols with about 3 to about 30, and preferably between about 5 to about 14 moles of ethylene oxide.

Many cationic surfactants are known in the art and almost any cationic surfactant having at least one long chain alkyl group of about 10 to 24 carbon atoms is suitable for optional use as a component in a composition comprising a *Hamelia patens* extract according to the present disclosure.

Other optional ingredients or additives which may be used in combination with *Hamelia patens* extract in formulating compositions according to the present disclosure include pH adjusting chemicals, for example, loweralkanolamines such as monoethanolamine (MEA) and triethanolamine (TEA). Sodium hydroxide solutions may also be utilized as an alkaline pH adjusting agent, as well as any organic acids, mineral acids or other acids known for their ability to adjust pH. The pH adjusting chemicals function to neutralize acidic or basic materials that may be present. Mixtures of more than one pH adjusting chemical can also be utilized, as well as buffers.

Phase regulants are well known and may also be optionally present in a composition of the disclosure. These can be represented by lower aliphatic alcohols having from 2 to 6 carbon atoms and from 1 to 3 hydroxyl groups, ethers of diethylene glycol and lower aliphatic monoalcohols having from 1 to 4 carbon atoms and the like.

Detergent hydrotropes may also be included in a composition according to the disclosure. Examples of detergent hydrotropes include salts of alkylarylsulfonates having up to 3 carbon atoms in the alkyl group e.g., sodium, potassium, ammonium, and ethanolamine salts of xylene, toluene, ethylbenzene, cumene, and isopropylbenzenesulfonic acids.

Other optional supplemental additives include de-foamers such as high molecular weight aliphatic acids, especially saturated fatty acids and soaps derived from them, dyes and perfumes; fluorescent agents or optical brighteners; suspension stabilizing agents; antioxidants; softening agents; uv-light inhibitors or absorbers; preservatives; polyacids, opacifiers, and bacteriacides.

An inorganic or organic builder may optionally be added to a composition according to some embodiments of the disclosure. Examples of inorganic builders include water-soluble alkali metal carbonates, bicarbonates, silicates and crystalline and amorphous alumino-silicates. Examples of organic builders include the alkali metal, alkaline metal, ammonium and substituted ammonium polyacetates, carboxylates, polycarboxylates, polyacetyl carboxylates and polyhydroxy sulfonates.

*Hamelia patens* extracts of the present disclosure are useful in providing compositions which contain materials typically known to and used by those skilled in the art of formulation as being useful in formulating skin-care compositions, shampoos and other products intended for topical application. For purposes of this disclosure, the words "materials typically known to and used by those skilled in the art of formulation" means one, or any combination comprising more than one of the materials selected from the group consisting of: fatty acids, alkyl sulfates, ethanolamines, amine oxides, alkali carbonates, water, ethanol, isopropanol, pine oil, sodium chloride, sodium silicate, polymers, alcohol alkoxylates, zeolites, aloe, vitamins, emu oil, anti-oxidants, carotenoids, terpenoids, flavonoids, hormones, perborate salts, alkali sulfates, enzymes, hydrotropes, dyes, fragrances, preservatives, brighteners, builders, polyacrylates, essential oils, alkali hydroxides, ether sulfates, alkylphenol ethoxylates, fatty acid amides, alpha olefin sulfonates, paraffin sulfonates, betaines, chelating agents, tallowamine ethoxylates, polyetheramine ethoxylates, ethylene oxide/propylene oxide block copolymers, alcohol ethylene oxide/propylene oxide low foam surfactants, methyl ester sulfonates, alkyl polysaccharides, N-methyl glucamides, alkylated sulfonate diphenyl oxide, and water soluble alkylbenzene sulfonates or alkyltoluene sulfonates, each present when selected in conventionally-used amounts to achieve their conventional function.

In some embodiments, any *Hamelia patens* extract of the present disclosure may be present in facial and body cleansing compositions. These cleansing compositions may also comprise a fatty acid soap together with other non-soap surfactants, such as mild synthetic surfactants. Body and facial cleaning compositions may also generally include a moisturizer or emollient and polymeric skin feel and mildness aids including dimethicone. The compositions may further optionally include thickeners (e.g., magnesium aluminum silicate, CARBOPOLS polymers), conditioners, water soluble polymers (e.g., carboxymethyl cellulose), dyes, hydrotrupes brighteners, perfumes, and germicides.

In some embodiments, any extract of *Hamelia patens* of the present disclosure may be present in a shampoo. The shampoo composition may also comprise one or more other surfactants, optionally a compound considered useful for treating dandruff, such as selenium sulfide, a suspending agent, an amide, nonionic polymer material for aiding in dispersing particles, nonvolatile silicone fluid, and a variety of other nonessential components suitable for rendering the composition more formulatable, such as preservatives, viscosity modifiers, pH adjusting chemicals, perfumes, and dyes.

In other embodiments, any *Hamelia patens* extract of the present disclosure may be present in a cosmetic composition, such as foundations, rouges, lipsticks, and lip balms. A cosmetic composition may further include at least one polymer thickening agent, one or more chemical preservatives or water activity depressants to prevent microbial spoilage, a sun-screening agent such as p-aminobenzoic acid, cinnamic acid derivatives, and a vehicle. The vehicle can include any dermatologically-acceptable diluent, dispersant or carrier useful in ensuring an even distribution of the composition when applied to human skin and may include water, an emollient such as an alcohol or oil, a propellant for example, trichloromethane, carbon dioxide or nitrous oxide, a humectant, and a powder such as chalk, talc, and starch.

In some embodiments, a salve, crème, ointment, emulsion, or lotion containing an extract of *Hamelia patens* according to the disclosure is applied topically to human skin, with gentle rubbing as per application of any other topical medicament. In some embodiments, a salve, crème, ointment, or lotion including a *Hamelia patens* extract according to the disclosure is applied once daily to such an area of skin nearby which pain associated with peripheral neuropathy is felt. In other embodiments, a salve, crème, ointment, or lotion including a *Hamelia patens* extract according to the disclosure is applied twice daily to such a skin area. In other embodiments, a salve, creme, ointment, or lotion including a *Hamelia patens* extract according to the disclosure is applied thrice daily to such a skin area. In other embodiments, a salve, crème, ointment, or lotion including a *Hamelia patens* extract according to the disclosure is applied four times daily to such a skin area. In other embodiments, a salve, creme, ointment, or lotion including a *Hamelia patens* extract according to the disclosure is applied more than four times daily, on an as-needed or as-desired basis to such a skin area. The foregoing treatment frequencies can be used with any topical composition containing *Hamelia patens* extract having the *Hamelia patens* extract present at any concentration level within the percentage ranges specified herein.

*Hamelia patens* extracts as provided herein, whether present in crystalline, amorphous, gummy or liquid form, including oil-based liquids, aqueous liquids or alcohol-water mixtures, and topical compositions, as described, are useful in combination with liposomes in a topical composition. Suitable liposomes include those recognized by those skilled in the art as being useful in combination with plant-derived extracts and components present therein as herein described to enhance delivery of such extracts or components into the dermal layers of a human subject. Liposomes include artificial microscopic vesicles consisting of an aqueous core present and enclosed within either one, or a plurality of phospholipid layers, which structured materials are useful to convey one or any combination including any number greater than one components present in *Hamelia patens* extract through the dermal layers when a composition of this disclosure includes liposomes in an effective amount.

*Hamelia patens* extracts as provided herein, whether present in crystalline form or liquid form, including oil-based liquids, aqueous liquids or alcohol-water mixtures, and topical compositions, as described, are useful in combination with nanoparticles in a topical composition. As used herein, a nanoparticle is any particulate form that is less than about one micrometer in at least one dimension, including particulate forms that are less than one micrometer in at least one dimension. Suitable nanoparticles include those recognized by those skilled in the art as being useful in combination with plant extracts and materials present in plant-derived extracts, and include without limitation such nanoparticles as: solid core nanoparticles, hollow core nanoparticles, lipid nanoparticles, polyethylene glycol ("PEG") nanoparticles, chitosan nanoparticles.

Below are set forth several examples of materials and methods useful in carrying out non-limiting exemplary embodiments of the invention. These examples are intended to be interpreted as being exemplary of various embodiments of this disclosure and not delimitive thereof, as one of ordinary skill in the art readily appreciates.

Example I

Petrolatum Extract of *Hamelia patens*

A one-liter volume of cut and cleaned leaves of *Hamelia patens* are compressed and combined with about 125 ml of petrolatum, the mixture being heated to about 65 degrees centigrade for about 10 minutes. The leafy material is mechanically separated from the petrolatum, which is optionally filtered, to afford a petrolatum-borne extract of the plant *Hamelia patens*.

Example II

Aqueous Alcohol Extract of *Hamelia patens*

500 grams of ground *Hamelia patens* leaves are combined with 500 ml of a solvent mixture that contains 10% by volume of ethanol in water. The liquid is maintained at room temperature for 30 minutes with occasional stirring of the leaves and solvent. The resulting solution is centrifuged to remove solids and filtered to provide a liquid extract of *Hamelia patens* in solution.

Example III

Crystalline Extract of *Hamelia patens*

The liquid extract provided in Example II is placed in a vacuum still, heated to fifty degrees centigrade, and subjected to reduced pressure of 300 torr with a slow sweep of nitrogen gas being admitted over the liquid to enhance removal of solvent, the pressure being maintained at 300 torr. Once the solvent has been removed, a crystalline extract of *Hamelia patens* remains. This extract is optionally purified via re-crystallization using an ethanol-water mixture.

Example IV

Topical Skin Lotion

Ten grams of the crystalline extract provided in Example III were placed in a 150 ml beaker. Ninety five grams of Vaseline® moisture locking lotion (unfragranced) were subsequently added to the beaker, and the contents mixed by mechanical means until the extract was substantially evenly dispersed within the lotion to provide a lotion containing 10% of an extract of the plant *Hamelia patens*. The concentration of *Hamelia patens* extract in the lotion is optionally adjusted to any desired level less than 10% by addition of and selected quantity more of the neat lotion.

Example V

Vitamin-Fortified Lotion

To forty five grams of the 10% lotion of example IV placed in a 100 ml beaker are added five grams of Vitamin E oil and the beaker contents mixed until at least substantially uniform to provide a Vitamin-fortified lotion.

Example VI

Lotion Concentrate

Fifty grams of the crystalline extract provided in Example III were placed in a 150 ml beaker. Fifty grams of Vaseline® moisture locking lotion (unfragranced) were subsequently added to the beaker, and the contents mixed by mechanical means until the extract was substantially evenly dispersed within the lotion to provide a lotion containing 50% of an extract of the plant *Hamelia patens*. This lotion may be used as a lotion concentrate suitable as a base stock from which other lotions may be produced.

Example VII

Salve Containing *Hamelia patens*

To 95 grams of a petrolatum-based extract of the plant *Hamelia patens* prepared according to example I, are added five grams of DMSO and 0.5 grams of soy lecithin. The mixture is blended until at least substantially uniform to provide a salve having enhanced transdermal mobility.

Example VIII

Oil in Water Emulsion

The following ingredients are blended together:

| | |
|---|---|
| fatty alcohols (50/50 mix C16 + C18) | 15 grams |
| mineral oil | 10 grams |
| petrolatum | 3 grams |
| PEG-15 (oleyl.cetyl alc.) | 5 grams |
| water | 67 grams |
| crystalline extract from example III | 7.5 grams |

Example IX

A topical composition described in Example IV, is modified to contain 5% of *Hamelia patens* extract by addition of further neat lotion. The 5% *Hamelia patens* lotion is suitable to be topically is applied to the skin of a subject experiencing pain associated with peripheral neuropathy. Such topical medicament composition can be topically applied as-needed to the skin in the region of where a person is suffering such pain, for symptomatic relief of said pain.

Example X

A topical composition described in Example IV, modified to contain 3% of *Hamelia patens* extract by addition of further neat lotion. The 3% *Hamelia patens* lotion is suitable to be topically applied to the skin of a subject experiencing pain associated with peripheral neuropathy on an ongoing basis. Such topical medicament composition can be topically applied as-needed to the skin in the region of where a person is suffering such pain, for symptomatic relief from said pain.

Example XI

A topical composition described in Example IV, modified to contain 1% of *Hamelia patens* extract by addition of further neat lotion. The 1% *Hamelia patens* lotion is suitable to be topically applied to the skin of a subject experiencing pain associated with peripheral neuropathy on an ongoing basis. Such topical medicament composition can be topically applied as-needed to the skin in the region of where a person is suffering such pain, for symptomatic relief from said pain.

Example XII

A topical composition described in Example IV, is modified to contain 15% of *Hamelia patens* extract by addition of crystalline *Hamelia patens* extract. The 15% *Hamelia patens* lotion is suitable to be topically applied to the skin of a subject experiencing pain associated with peripheral neuropathy on an ongoing basis. Such topical medicament composition can be topically applied as-needed to the skin in the region of where a person is suffering such pain, for symptomatic relief from said pain.

One type of peripheral neuropathy that is a known specific diagnosis is diabetic neuropathy, resulting from diabetes mellitus. Diabetic neuropathy can affect all the peripheral nerves including sensory pain fibers, motor neurons, and the autonomic nervous system. The small sensory nerves lie close to the surface of the skin and are readily available to topical treatment. The patient can experience any combination of symptoms.

Pre-diabetic peripheral neuropathy is another specific diagnosis, and it shares the same cause as peripheral neuropathy that results from diabetes mellitus, but at an earlier stage in the progression of the diabetes. This pain is caused by nerve damage as a result of the effects of high blood sugar and attendant poor circulation and the loss of nerve fibers over time causes nerves to lose their ability to transmit sensation, often resulting in numbness.

Peripheral neuropathy resulting from chronic alcoholism is a known specific diagnosis that is due to a person consuming excessive amounts of alcohol to the point where the peripheral nerves become damaged, disabling them from being able to transmit signals between the body, spinal cord, and brain. Alcohol-induced peripheral neuropathy can effect bowel and urinary elimination, walking, sexual arousal, arm and leg movement, and speech. Symptoms include numbness, tingling and burning, prickly sensations, muscle spasms and cramps, muscle weakness and atrophy, loss of muscle function, and movement disorders.

Peripheral neuropathy resulting from compression is a known specific diagnosis that occurs when nerves become compressed. The compression may occur as a result of trauma, inflammation or entrapment. One of the most common types of compression neuropathy is Carpal Tunnel Syndrome.

Peripheral neuropathy following chemotherapy treatments is a known specific diagnosis that is due to some chemotherapeutic drugs causing damage to nerves that control sensations and movements of the arms and legs.

Peripheral neuropathy following physical trauma is a known specific diagnosis that is due to sudden traumas, such as encountered in automobile accidents, falls or sports injuries, or other traumas that sever or damage peripheral nerves.

Examples XIII through XVIII are illustrative of successful use of a topical composition comprising *Hamelia patens* extract in combination with a dermatologically-acceptable carrier in treating peripheral neuropathy. The topical composition used in each of the Examples XIII through XVIII used CETAPHIL@ gentle skin cleanser (Galderma Laboratories) as the dermatologically-acceptable carrier, the *Hamelia patens* extract was produced according to Example III, and the concentration of *Hamelia patens* extract in the topical compositions used was 10% by weight based on the total weight of the topical composition.

Example XIII

Pre-Diabetic Peripheral Neuropathy

A 70 year old Caucasian male subject was suffering from pain and numbness in both forefeet due to Peripheral Neuropathy caused by elevated glucose levels (HGB A1C was 6.5%) from pre-diabetes. Conventional treatment including a steroid cream and anti-inflammatory pain meds did not relive the subject's pain. A salve containing 10% *Hamelia patens* extract was applied by the subject topically to the affected area of the feet twice daily for 30 days. The subject noted immediate and prompt relief of pain and numbness shortly after the first application of the salve. Use of the salve was continued on an as-needed basis by the subject.

Example XIV

Diabetes Mellitus Insulin Dependent Peripheral Neuropathy

A 75 year old Caucasian male subject was suffering from pain and numbness of both feet due to Peripheral Neuropathy secondary to insulin dependent Diabetes mellitus. Pain was so severe that sleep was denied from chronic pain. Even conventional pain medicines did not help. A salve containing 10% *Hamelia patens* extract was applied twice daily by the patient to his skin near the painful area, and the subject experienced immediate pain and numbness relief in both feet. Thereafter the subject achieved restful sleep. Subject continues to use the salve for relief successfully.

Example XV

Chronic Alcoholism-Induced Peripheral Neuropathy

A 50 year old Caucasian male was suffering from pain and numbness in both lower extremities due to Peripheral Neuropathy induced by chronic alcoholism. Conventional medicines of pain killers and anti-seizure medications did not work to relieve the subject's pain. The subject applied a salve containing a 10% *Hamelia patens* extract to the skin of his feet twice daily for two weeks. The subject experienced immediate pain and numbness relief. The subject continues to relieve his pain with daily use of the salve.

Example XVI

Compression Neuropathy (HNP)

A 50 year old Caucasian male was suffering from chronic pain and numbness of his left foot after an accident that caused a herniated nucleus pulposis disc injury, resulting in peripheral neuropathy of left foot. Conventional medicine of opioids and tri-cyclic anti-depressants did not relieve his pain. The subject applied a salve of 10% *Hamelia patens* extract to the skin of his left foot twice daily and promptly experienced good relief of pain and numbness in the left foot. The subject continues to experience good relief of symptoms with topical use of the salve.

Example XVII

Post Chemotherapy Breast Cancer Treatment Peripheral Neuropathy

A 52 year old Caucasian female underwent chemotherapy treatments for breast cancer. She later developed pain and numbness of her feet caused by peripheral neuropathy from chemotherapy. She tried conventional medications for peripheral neuropathy of anti-seizure without benefit. She applied a salve containing a 10% *Hamelia patens* extract to the skin of her feet and had immediate pain relief. She continues to use the salve with good success.

Example XVIII

Post-Traumatic Peripheral Neuropathy

A 52 year old Caucasian female underwent malignant tumor surgical excision and then subsequently developed pain and numbness of the right foot. In addition chemotherapy was given for cancer treatment. She tried conventional pain relievers, tri-cyclic anti-depressants, and seizure medications without relief. She applied a salve containing 10% *Hamelia patens* extract to the skin of her right foot and it gave prompt relief from the pain. She still continues to use the salve successfully.

Quick relief of pain associated with peripheral neuropathy has thus been demonstrated using a topical medicament comprising an extract of *Hamelia patens* in combination with a dermatologically-acceptable carrier, when the topical medicament is contacted with human skin at or near the site of the pain. Typical application frequencies for a topical medicament according to this disclosure is two to three times daily; however, the topical medicament can be applied on an "as-needed" basis by the person suffering from such pain. Following application of a topical medicament according to this disclosure, the subject notices almost immediate relief of the pain caused by specific conditions of peripheral neuropathy. The relief from the pain is significant to the subject in that they can thereafter rest comfortably and may be able to even obtain restful sleep. Pain typically returns hours after application of the topical medicament, requiring reapplication of the topical medicament, presumably due to the integral and organic nature of the cause of the pain. The mechanism of action of a topical medicament and process of using according to this invention is not understood.

The present inventor is a retired Medical Doctor and individually possesses the diagnosis of peripheral neuropathy that is mildly symptomatic of neurological symptoms in both feet in the fore foot area. Symptoms experienced by the inventor are in the category of sensory disturbances in the form of numbness, tingling with dysthesia in fore feet (abnormal sensation to body part). The clinical diagnosis was confirmed in results of nerve conduction tests which showed mild polyneuropathy of a symmetrical distribution of the lower extremities presumably caused by an abnormal glucose tolerance. The inventor's symptoms are very nicely treated successfully by topical application of 10% *Hamelia patens* extract in a dermatologically-acceptable carrier once daily to the affected areas of his feet. The pain symptoms are completely abated with this treatment without side-effects or lifestyle disturbances. The inventor is under the care of an American board-certified endocrinologist. I believe the present invention to be a medical breakthrough due to, inter alia: 1) the affability of the methods taught herein being patient-friendly; 2) the availability of the method by easy topical applications without resorting to systemic side effects; and 3) the ability in high efficacy to provide immediate relief in the treatment armamentarium for peripheral neuropathy, which represents a common and difficult condition to successfully treat for many individuals. The method(s) taught herein are superior to currently-available regimens in medicine, as current regimens possess many untoward side effects and pharmaceutical efficacy is not high. The present invention fulfills a long-standing, un-met need in the medical arts.

Although the topical medicament skin lotion used in the above examples illustrating treatment of pain associated with peripheral neuropathy contained *Hamelia patens* extract at a concentration of 10% by weight, other concentrations of *Hamelia patens* extract in a skin creme, lotion, salve, gel or other dermatologically-acceptable carrier are suitable for use according to this invention to achieve like results. Without limitation, any topical composition comprising a dermatologically-acceptable carrier in combination with *Hamelia patens* extract wherein the concentration of *Hamelia patens* extract in the topical composition is any concentration in the range of between 1.0% and 20.0%, including all percentages and ranges of percentages therebetween, is sufficient for use in relieving pain associated with peripheral neuropathy according to some embodiments this invention. Thus, in some embodiments, any concentration of *Hamelia patens* extract in a dermatologically-acceptable carrier in the range of between 5.0% and 15.0%, including all percentages and ranges of percentages therebetween, are sufficient amounts for use in relieving pain associated with peripheral neuropathy.

After reading this specification, one of ordinary skill recognizes, combined with what is known in the art, that various application regimens for a topical composition described herein are possible, as in the case of many other topically-applied materials. It is a matter of routine experimentation for example, to apply a topical composition any number of times per day as desired, and using any selected concentration of *Hamelia patens* extract in a topical composition. According to some embodiments, a topical composition comprising *Hamelia patens* extract in combination with a dermatologically-acceptable carrier having any amount of *Hamelia patens* extract present between 1% and 20% by weight of the topical composition, including all percentages and ranges of percentages therebetween, can be applied to human skin for relief of pain associated with peripheral neuropathy any number of selected or desired times per day including without limitation once daily, twice daily, three times daily, four times daily, five times daily and six times daily. Methods of the invention can be practiced by persons who are either male or female. In some embodiments methods of the invention are applied to female subjects who are either peri-menopausal, menopausal, or post-menopausal.

Although this invention has been described and disclosed in relation to various embodiments, modifications, combinations, and alterations of the features of various embodiments disclosed become apparent to persons of ordinary skill in this art after reading and understanding the teachings of this specification, and the claims appended hereto in view of the knowledge of one skilled in the art. The present disclosure includes subject matter defined by any combinations of any one (or more) of the features, elements, or aspects present described in reference to any embodiment described in this disclosure with one or more feature(s), element(s), or aspect(s) described in relation to any other one (or more) other embodiments described. These combinations include the incorporation of the features and/or aspect(s) of any dependent claim, singly or in combination with features and/or limitations of any one or more than one of the other dependent claims, with features and/or limitations of any one or more than one independent claim(s), with the remaining dependent claims in their original text being read and applied to any independent claim(s) so modified. These combinations also include combination of the features and/or limitations of one or more of the independent claims with features and/or limitations of another one or more than one of the independent claims to arrive at a modified independent claim, with the remaining dependent claims in their original text or alternately as modified per the foregoing, being read and applied to any independent claim(s) so modified.

The invention claimed is:

1. A method for providing symptomatic relief of pain associated with peripheral neuropathy in a human subject experiencing such pain, said method comprising:
   a) providing a topical composition containing *Hamelia patens* extract in combination with a dermatologically-acceptable carrier, said *Hamelia patens* extract being present in said topical composition in any amount between 1.0% and 20.0% by weight based on the total weight of said topical composition;
   b) applying said composition topically to the skin of said human subject sufficiently to relieve said pain.

2. A method according to claim 1 wherein said composition is applied to the skin of said subject twice per day.

3. A method according to claim 1 wherein said *Hamelia patens* extract is present in said topical composition in any amount between 5% and 15% by weight based on the total weight of said topical composition.

4. A method according to claim 1 wherein said peripheral neuropathy is pre-diabetic peripheral neuropathy.

5. A method according to claim 1 wherein said peripheral neuropathy is from diabetes mellitus.

6. A method according to claim 1 wherein said peripheral neuropathy is from chronic alcoholism.

7. A method according to claim 1 wherein said peripheral neuropathy is a compression neuropathy.

8. A method according to claim 1 wherein said peripheral neuropathy is post-chemotherapy peripheral neuropathy.

9. A method according to claim 1 wherein said peripheral neuropathy is post-traumatic peripheral neuropathy.

10. A method according to claim 1 wherein said topical composition comprises at least one material selected from the group consisting of: alkaloids, 2-alpha-hydroxyursolic acid, apigenin-7-o-beta d-glucuronide, aricine, catequine, 19-alphahydroxy Asiatic acid, 24-methylenecycloartane-3β-ol, 24-methylcycloart-24-en-3β-ol, 2E-3,7,11,15,19-pentamethyl-2-eicosane-1-ol, ephedrine, flavonones, 2'-5-5'-7-tetrahydroxy-7-o-rutinoside, isomaruquine, isopteropodine, maruquine, the methyl ester of maruquine, mitraphylline, narirutin, narirutin (2r), narirutin (2s), oxindole alkaloids, oxindole aricine, palmirine, pigenin-7-o-beta D-glucuronide, pomolic acid, pteropodine, rumberine, rosmarinic acid, rotundic acid, rumberine, rutin, seneciophylline, 8-sitosterol, speciophylline, stigmast-4-en-3-3-dione, stigmast-4-en-3-6-dione, stigmasterol, tannins, tormentic acid, uncarine F, and ursolic acid, and including any mixtures of any of the foregoing.

11. Method according to claim 10 wherein said composition comprises all of said materials recited in said group.

12. Method according to claim 10 wherein any one, or any combination including more than one, of said materials in said group are omitted from said composition.

13. Method according to claim 10 wherein each of said materials of said group that are present are each independently present in any amount between about 0.05% by weight and about 30% by weight based on the weight of the Hamelia patens extract present in said composition.

14. Method according to claim 1, wherein said dermatologically-acceptable carrier is in any form selected from the group consisting of: salves, creams, ointments, gels, and lotions.

15. Method according to claim 14 wherein said dermatologically-acceptable carrier comprises an emulsion.

16. Method according to claim 1 wherein said dermatologically-acceptable carrier comprises any material selected from the group consisting of: water; saline solution, any C1 to C4 alcohol; any glyceryl ester oil; and any mineral oil, including any combinations thereof.

17. Method according to claim 1 wherein said topical composition comprises a nanoparticle.

18. Method according to claim 17 wherein said nanoparticle is selected from the group consisting of: solid core nanoparticles, hollow core nanoparticles, lipid nanoparticles, polyethylene glycol nanoparticles, and chitosan nanoparticles, including any mixtures thereof.

19. Method according to claim 1 wherein said topical composition comprises a liposome.

20. Method according to claim 1 wherein said extract is selected from the group consisting of: an aqueous extract of Hamelia patens, a non-aqueous extract of Hamelia patens, an alcoholic extract of Hamelia patens, an aqueous-alcoholic extract of Hamelia patens, and any mixtures of the foregoing.

* * * * *